United States Patent
Chuang

(10) Patent No.: US 11,202,776 B2
(45) Date of Patent: Dec. 21, 2021

(54) TREATMENT OF GASTROPARESIS WITH TRIAZASPIRO[4.5]DECANONE

(71) Applicant: Millennium Pharmaceuticals, Inc., Cambridge, MA (US)

(72) Inventor: Emil Chuang, Cambridge, MA (US)

(73) Assignee: Takeda Pharmaceutical Company Limited

( * ) Notice: Subject to any disclaimer, the term of this patent is extended or adjusted under 35 U.S.C. 154(b) by 38 days.

(21) Appl. No.: 16/610,863

(22) PCT Filed: May 11, 2018

(86) PCT No.: PCT/US2018/032270
§ 371 (c)(1),
(2) Date: Nov. 4, 2019

(87) PCT Pub. No.: WO2018/209201
PCT Pub. Date: Nov. 15, 2018

(65) Prior Publication Data
US 2020/0155523 A1    May 21, 2020

Related U.S. Application Data

(60) Provisional application No. 62/505,662, filed on May 12, 2017, provisional application No. 62/547,686, filed on Aug. 18, 2017.

(51) Int. Cl.
*A61K 31/438* (2006.01)
*A61P 1/14* (2006.01)

(52) U.S. Cl.
CPC .............. *A61K 31/438* (2013.01); *A61P 1/14* (2018.01)

(58) Field of Classification Search
CPC ................................ A61K 31/438; A61P 1/00
USPC .......................................................... 514/278
See application file for complete search history.

(56) References Cited

U.S. PATENT DOCUMENTS

2012/0010228 A1 * 1/2012 Luehr et al. ......... A61K 31/438
514/278

* cited by examiner

*Primary Examiner* — Charanjit Aulakh
(74) *Attorney, Agent, or Firm* — Honigman LLP; Lucy X. Yang; Jonathan P. O'Brien

(57) ABSTRACT

Provided herein is a method of treating or alleviating one or more symptoms of a disorder, disease, or condition mediated by a dopamine $D_2$ or $D_3$ receptor with 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof. Also provided herein is a method of increasing the serum prolactin level with 3-((1-cyclohexyl-4-oxo-8-(4-oxo-4-phenylbutyl)-1,3,8-triazaspiro[4.5]decan-3-yl) methyl)benzoic acid or a pharmaceutically acceptable salt thereof.

23 Claims, 3 Drawing Sheets

TREATMENT OF GASTROPARESIS WITH TRIAZASPIRO[4.5]DECANONE

CROSS REFERENCE TO RELATED APPLICATIONS

This application is a National Stage of International Application No. PCT/US2018/032270, filed May 11, 2018; which claims the benefit of U.S. Provisional Application No. 62/505,662, filed May 12, 2017, and U.S. Provisional Application No. 62/547,686, filed Dec. 21, 2017; the disclosure of each of which is incorporated by reference in its entirety.

FIELD

Provided herein is a method of treating or alleviating one or more symptoms of a disorder, disease, or condition mediated by a dopamine $D_2$ or $D_3$ receptor with 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof. Also provided herein is a method of increasing the serum prolactin level in a subject with 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof.

BACKGROUND

Gastroparesis is a disorder of the stomach characterized by delayed gastric emptying in the absence of mechanical obstruction. Symptoms, including nausea, vomiting, early satiety, abdominal pain, and postprandial fullness, are chronic with episodic symptom exacerbation. Parkman et al., *Gastroenterology* 2004, 127, 1592-1622. The prevalence of gastroparesis in the United States is 24.2 per 100,000. Camilleri et al., *Am. J. Gastroenterol.* 2013, 108, 18-37. In cases of chronic gastroparesis, diabetic (29%), postsurgical (13%), and idiopathic (36%) etiologies comprise the majority of cases in the tertiary referral setting. Hyett et al., *Gastroenterology* 2009, 137, 445-452. Gastroparesis can result in nutritional compromise, impaired glucose control, and a poorer quality of life, independent of other factors such as age, tobacco and alcohol use, or types of diabetes. Choung et al., *Am. J. Gastroenterol.* 2012, 107, 82-88. The impact of gastroparesis as a serious outcome on day-to-day functioning is well-document both in terms of patients' deteriorating quality of life, and the direct or indirect economic burdens placed on society. Parkman et al., *Neurogastroenterol. Motil.* 2010, 22, 113-133.

Currently in the United States, there are no approved therapies for the chronic treatment of diabetic or idiopathic gastroparesis. Metoclopramide is a FDA-approved medication for the short term treatment of acute and recurrent diabetic gastroparesis. Lee and Kuo, *Expert. Rev. Endocrinol. Metab.* 2010, 5, 653-662. However, its dosage and duration of treatment are limited by its well-documented toxicities, the most notable of which is a category of movement disorders known as extrapyramidal symptoms (EPS). Id.; Meltzer, *Ann. Rev. Med.* 2013, 64, 393-406. Of greatest concern is tardive dyskinesia, a severe and often irreversible EPS. The risk of developing tardive dyskinesia increases with dose level and duration of treatment. Lee and Kuo, *Expert. Rev. Endocrinol. Metab.* 2010, 5, 653-662. Thus, the package insert of metoclopramide in the United States includes a black box warning regarding its chronic use for longer than 12 weeks. Id. Domperidone is marketed for use as an anti-emetic and prokinetic agent in a number of countries worldwide, although not in the United States due to its cardiovascular safety profile, which includes a risk for drug-induced long QT syndrome, torsades de pointes, and sudden cardiac death. Michaud and Turgeon, *Cardiovasc. Pharmacol.* 2013, 61, 215-217. Owing to safety concerns, both metoclopramide and domperidone are restricted to short term use of less than a week. See, e.g., Metoclopramide 10 mg Tablets: Summary of Product Characteristics; Barnstable, North Devon, UK: Actavis UK Ltd., Revised 19 Oct. 2016; and Domperidone 10 mg Film-Coated Tablets: Summary of Product Characteristics; Wrexham, UK: Wockhardt UK Ltd., Revised 14 Jun. 2016. Therefore, there is a need for an effective therapy for gastroparesis.

SUMMARY OF THE DISCLOSURE

Provided herein is a method of treating or alleviating one or more symptoms of a disorder, disease, or condition mediated by a dopamine $D_2$ or $D_3$ receptor in a subject, comprising administering to the subject 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof, or a pharmaceutically acceptable solvate or hydrate thereof.

Also provided herein is a method of treating or alleviating one or more symptoms of gastroparesis in a subject, comprising administering to the subject 3-((1-cyclohexyl-4-oxo-8-(4-oxo-4-phenylbutyl)-1,3,8-triazaspiro[4.5]decan-3-yl) methyl)benzoic acid or a pharmaceutically acceptable salt thereof, or a pharmaceutically acceptable solvate or hydrate thereof.

Furthermore, provided herein is a method of treating or alleviating one or more symptoms of a disorder, disease, or condition characterized by delayed gastric emptying in a subject, comprising administering to the subject 3-((1-cyclohexyl-4-oxo-8-(4-oxo-4-phenylbutyl)-1,3,8-triazaspiro [4.5]decan-3-yl)methyl)benzoic acid or a pharmaceutically acceptable salt thereof, or a pharmaceutically acceptable solvate or hydrate thereof.

Provided herein is a method of enhancing gastrointestinal motility in a subject, comprising administering to the subject 3-(1-cyclohexyl-4-oxo-8-(4-oxo-4-phenylbutyl)-1,3,8-triazaspiro[4.5]decan-3-yl)methyl)benzoic acid or a pharmaceutically acceptable salt thereof, or a pharmaceutically acceptable solvate or hydrate thereof.

Provided herein is a method of increasing the serum prolactin level in a subject, comprising administering to the subject 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof, or a pharmaceutically acceptable solvate or hydrate thereof.

DETAILED DESCRIPTION

Figure 1:
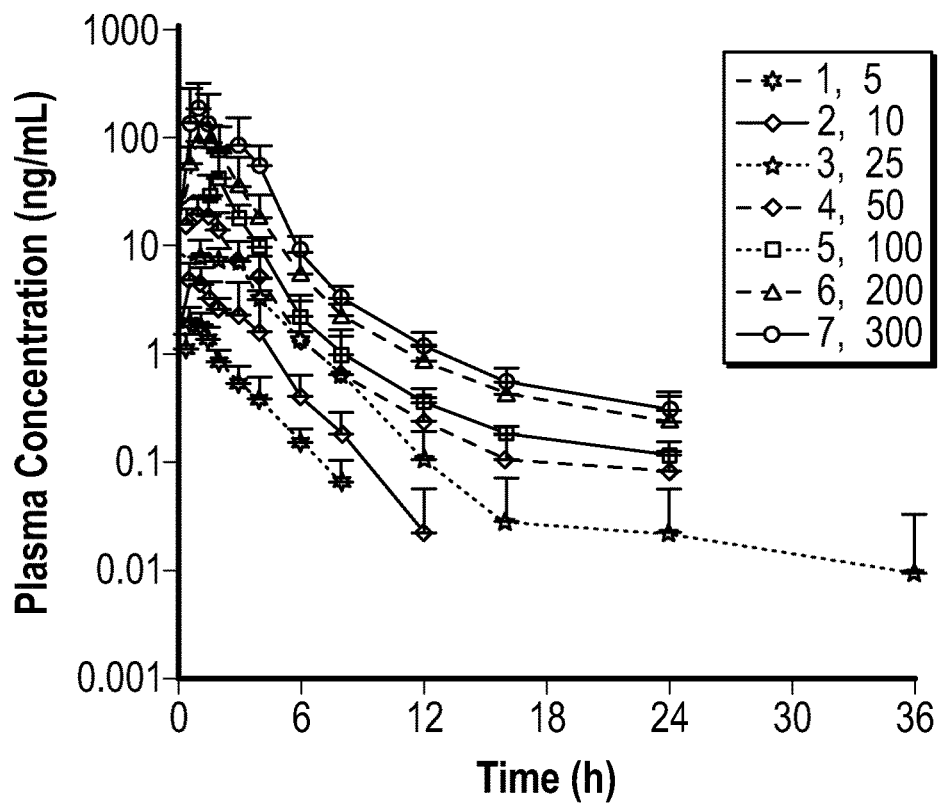
FIG. 1 shows mean plasma concentration-time profiles of 3-((1-cyclohexyl-4-oxo-8-(4-oxo-4-phenylbutyl)-1,3,8-triazaspiro[4.5]decan-3-yl)methyl)benzoic acid in fasting subjects following a single PO dose.

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.: Philadelphia, Pa., 2012; *Handbook of Pharmaceutical Excipients,* 7th ed.; Rowe et al., Eds.; The Pharmaceutical Press and the American Pharmaceutical Association: 2012; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "solvate" refers to a complex or aggregate formed by one or more molecules of a solute, e.g., a compound described herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

Methods of Use

In one embodiment, provided herein is a method of treating or alleviating one or more symptoms of a disorder, disease, or condition mediated by a dopamine $D_2$ or $D_3$ receptor in a subject, comprising administering to the subject 3-((1-cyclohexyl-4-oxo-8-(4-oxo-4-phenylbutyl)-1,3,8-triazaspiro[4.5]decan-3-yl)methyl)benzoic acid (hereinafter, "Compound 1") or a pharmaceutically acceptable salt thereof, or a pharmaceutically acceptable solvate or hydrate thereof.

In another embodiment, provided herein is a method of treating or alleviating one or more symptoms of a disorder, disease, or condition mediated by a dopamine $D_2$ or $D_3$ receptor in a subject, comprising administering to the subject a therapeutically effective amount of Compound 1 or a pharmaceutically acceptable salt thereof, or a pharmaceutically acceptable solvate or hydrate thereof.

In certain embodiments, the disorder, disease, or condition is mediated by a dopamine $D_2$ receptor. In certain embodiments, the disorder, disease, or condition is mediated by a dopamine $D_3$ receptor. In certain embodiments, the disorder, disease, or condition is mediated by dopamine $D_2$ and $D_3$ receptors.

In certain embodiments, the disorder, disease, or condition mediated by a dopamine $D_2$ or $D_3$ receptor is a gastrointestinal disease. In certain embodiments, the disorder, disease, or condition mediated by a dopamine $D_2$ or $D_3$ receptor is constipation, dyspepsia, functional dyspepsia, gastroesophageal reflux disease (GERD), gastroparesis (also known as gastric stasis), heartburn, irritable bowel syndrome (IBS), opioid-induced ileus, postoperative ileus, postprandial distress syndrome, or visceral hypersensitivity. In certain embodiments, the disorder, disease, or condition mediated by a dopamine $D_2$ or $D_3$ receptor is chronic unexplained nausea and vomiting, cyclic vomiting syndrome, drug induced nausea, or postoperative nausea and vomiting. In certain embodiments, the disorder, disease, or condition mediated by a dopamine $D_2$ or $D_3$ receptor is a gastrointestinal motility disorder. In certain embodiments, the disorder, disease, or condition mediated by a dopamine $D_2$ or $D_3$ receptor is gastroparesis. In certain embodiments, the disorder, disease, or condition mediated by a dopamine $D_2$ or $D_3$ receptor is diabetic gastroparesis. In certain embodiments, the disorder, disease, or condition mediated by a dopamine $D_2$ or $D_3$ receptor is symptomatic diabetic gastroparesis. In certain embodiments, the disorder, disease, or condition mediated by a dopamine $D_2$ or $D_3$ receptor is idiopathic gastroparesis. In certain embodiments, the disorder, disease, or condition mediated by a dopamine $D_2$ or $D_3$ receptor is symptomatic idiopathic gastroparesis. In certain embodiments, the disorder, disease, or condition mediated by a dopamine $D_2$ or $D_3$ receptor is gastroparesis associated with Parkinson disease, cancer, a viral infection, or a connective tissue disease. In certain embodiments, the disorder, disease, or condition mediated by a dopamine $D_2$ or $D_3$ receptor is gastroparesis associated with a gastric surgery, including, but not limited to, gastrectomy, gastric bypass, gastric banding, bariatric endoscopy, pyloroplasty, vagotomy, or fundoplication. In certain embodiments, the disorder, disease, or condition mediated by a dopamine $D_2$ or $D_3$ receptor is gastroparesis associated with a gastric surgery that manipulates the natural anatomy of the stomach. In certain embodiments, the disorder, disease, or condition mediated by a dopamine $D_2$ or $D_3$ receptor is gastroparesis associated with a medication that affects gastric emptying, including, but not limited to, opioids, glucagon-like peptide-1 analogs (e.g., exenatide and liraglutide), amylin analogs (e.g., pramlintide), and cannabinoids.

In certain embodiments, the symptom of the disorder, disease, or condition mediated by a dopamine $D_2$ or $D_3$ receptor is abdominal pain, belching, bloating, early satiety, epigastric pain or discomfort, excess gas, heartburn, loss of appetite, nausea, postprandial fullness, regurgitation, swollen abdomen, vomiting, or a combination thereof. In certain embodiments, the symptom of the disorder, disease, or condition mediated by a dopamine $D_2$ or $D_3$ receptor is abdominal pain, bloating, early satiety, epigastric pain or discomfort, nausea, postprandial fullness, vomiting, or a combination thereof. In certain embodiments, the symptom of the disorder, disease, or condition mediated by a dopamine $D_2$ or $D_3$ receptor is belching, bloating, heartburn, indigestion, nausea, regurgitation, vomiting, or a combination thereof. In certain embodiments, the symptom of the disorder, disease, or condition mediated by a dopamine $D_2$ or $D_3$ receptor is epigastric pain, diffuse abdominal pain, or pain associated with bowel movement.

In one embodiment, provided herein is a method of treating or alleviating one or more symptoms of a disorder, disease, or condition characterized by delayed gastric emptying in a subject, comprising administering to the subject 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof, or a pharmaceutically acceptable solvate or hydrate thereof.

In one embodiment, the disorder, disease, or condition characterized by delayed gastric emptying is a disorder, disease, or condition mediated by a dopamine $D_2$ or $D_3$ receptor. In another embodiment, the disorder, disease, or condition characterized by delayed gastric emptying is gastroparesis.

In one embodiment, provided herein is a method of treating or alleviating one or more symptoms of gastroparesis in a subject, comprising administering to the subject: Compound 1 or a pharmaceutically acceptable salt thereof, or a pharmaceutically acceptable solvate or hydrate thereof.

In another embodiment, provided herein is a method of treating or alleviating one or more symptoms of gastroparesis in a subject, comprising administering to the subject: a therapeutically effective amount of Compound 1 or a pharmaceutically acceptable salt thereof, or a pharmaceutically acceptable solvate or hydrate thereof.

In certain embodiments, the gastroparesis is diabetic gastroparesis. In certain embodiments, the gastroparesis is symptomatic diabetic gastroparesis. In certain embodiments, the gastroparesis is idiopathic gastroparesis. In certain embodiments, the gastroparesis is symptomatic idiopathic gastroparesis.

In certain embodiments, the symptom of gastroparesis is abdominal pain, belching, bloating, early satiety, epigastric pain or discomfort, excess gas, heartburn, loss of appetite, nausea, postprandial fullness, regurgitation, swollen abdomen, vomiting, or a combination thereof. In certain embodiments, the symptom of gastroparesis is abdominal pain, bloating, early satiety, epigastric pain or discomfort, nausea, postprandial fullness, vomiting, or a combination thereof. In certain embodiments, the symptom of gastroparesis is belching, bloating, heartburn, indigestion, nausea, regurgitation, vomiting, or a combination thereof.

In one embodiment, provided herein is a method of treating or alleviating gastroparesis accompanied with nausea, vomiting, early satiety, abdominal pain, postprandial fullness or a combination thereof in a subject, comprising administering to the subject 3-((1-cyclohexyl-4-oxo-8-(4-oxo-4-phenylbutyl)-1,3,8-triazaspiro[4.5]decan-3-yl) methyl)benzoic acid or a pharmaceutically acceptable salt thereof, or a pharmaceutically acceptable solvate or hydrate thereof.

In one embodiment, provided herein is a method of enhancing gastrointestinal motility in a subject, comprising administering to the subject 3-((1-cyclohexyl-4-oxo-8-(4-oxo-4-phenylbutyl)-1,3,8-triazaspiro[4.5]decan-3-yl) methyl)benzoic acid or a pharmaceutically acceptable salt thereof, or a pharmaceutically acceptable solvate or hydrate thereof.

In one embodiment, provided herein is a method of increasing the serum prolactin level in a subject, comprising administering to the subject 3-((1-cyclohexyl-4-oxo-8-(4-oxo-4-phenylbutyl)-1,3,8-triazaspiro[4.5]decan-3-yl) methyl)benzoic acid or a pharmaceutically acceptable salt thereof, or a pharmaceutically acceptable solvate or hydrate thereof.

In another embodiment, provided herein is a method of increasing the serum prolactin level in a subject, comprising administering to the subject a therapeutically effective amount of 3-((1-cyclohexyl-4-oxo-8-(4-oxo-4-phenylbutyl)-1,3,8-triazaspiro[4.5]decan-3-yl)methyl)benzoic acid or a pharmaceutically acceptable salt thereof, or a pharmaceutically acceptable solvate or hydrate thereof.

In certain embodiments, Compound 1, or a pharmaceutical acceptable solvate or hydrate thereof, is administered in a sufficient amount to increase the serum prolactin level to a concentration ranging from about 10 to about 500 ng/mL, from about 10 to about 200 ng/mL, from about 20 to about 200 ng/mL, or from about 50 to about 200 ng/mL.

Compound 1, i.e., 3-((1-cyclohexyl-4-oxo-8-(4-oxo-4-phenylbutyl)-1,3,8-triazaspiro[4.5]decan-3-yl)methyl)benzoic acid, has the following structure:

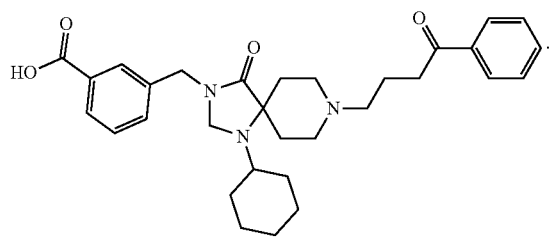 [SMILES: O=C(O)c1cccc(CN2CN(C3CCCCC3)C3(CCN(CCCC(=O)c4ccccc4)CC3)C2=O)c1]

In certain embodiments, Compound 1 is prepared according to the procedures as described in U.S. Pat. No. 8,691,836 or 9,156,940, the disclosure of each of which is incorporated herein by reference in its entirety.

In certain embodiments, Compound 1 is administered as a pharmaceutically acceptable salt, or a pharmaceutically acceptable solvate or hydrate thereof. In certain embodiments, Compound 1 is administered as a pharmaceutically acceptable salt with an acid, or a pharmaceutically acceptable solvate or hydrate thereof. In certain embodiments, the acid is selected from: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecyl sulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In certain embodiments, Compound 1 is administered as a pharmaceutically acceptable salt with a maleic acid (i.e., a maleate salt), or a pharmaceutically acceptable solvate or hydrate thereof; in one embodiment, the molar ratio of maleic acid to Compound 1 is about 1.

In certain embodiments, Compound 1 is administered as a pharmaceutically acceptable salt with a base, or a pharmaceutically acceptable solvate or hydrate thereof. In certain embodiments, the base is selected from: calcium hydroxide, magnesium hydroxide, potassium hydroxide, sodium hydroxide, zinc hydroxide, L-argentine, benethamine, benzathine, choline, decanal, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

In certain embodiments, Compound 1 is administered at a dosage ranging from about 1 to about 500, from about 2 to about 300, from about 5 to about 200, or from about 5 to about 100 mg per day as measured in the amount of free Compound 1 or a maleate salt thereof. In certain embodiments, Compound 1 is administered at a dosage of about 5, about 10, about 25, about 50, about 100, about 200, or about 300 mg per day as measured in the amount of free Compound 1 or a maleate salt thereof. In certain embodiments, Compound 1 is administered at a dosage of about 5, about 10, about 15, about 20, about 25, about 30, about 35, about 40, about 45, about 50, about 60, about 70, about 80, about 90, about 100, about 110, about 120, about 130, about 140, or about 150 mg per day as measured in the amount of free Compound 1 or a maleate salt thereof. In certain embodiments, Compound 1 is administered at a dosage of about 5, about 10, about 25, about 50, about 100, about 200, or about 300 mg per day as measured in the amount of free Compound 1 or a maleate salt thereof. In certain embodiments, Compound 1 is administered at a dosage of about 10, about 25, about 50, or about 200 mg per day as measured in the amount of free Compound 1 or a maleate salt thereof. In certain embodiments, Compound 1 is administered at a dosage of about 5, about 25, or about 50 mg twice daily as measured in the amount of free Compound 1 or a maleate salt thereof. In certain embodiments, Compound 1 is administered at a dosage of about 5 mg twice daily as measured in the amount of free Compound 1 or a maleate salt thereof up to 12 weeks. In certain embodiments, Compound 1 is administered at a dosage of about 25 mg twice daily as measured in the amount of free Compound 1 or a maleate salt thereof up to 12 weeks. In certain embodiments, Compound 1 is administered at a dosage of about 50 mg twice daily as measured in the amount of free Compound 1 or a maleate salt thereof up to 12 weeks.

In certain embodiments, Compound 1 is administered at a dosage ranging from about 1 to about 250, from about 1 to about 200, from about 1 to about 100, or from about 2 to about 50 mg per day as measured in the amount of free Compound 1 or a maleate salt thereof. In certain embodiments, Compound 1 is administered at a dosage of about 1, about 2, about 5, about 10, about 15, about 20, about 25, about 30, about 35, about 40, about 45, about 50 mg per day as measured in the amount of free Compound 1 or a maleate salt thereof. In certain embodiments, Compound 1 is administered at a dosage of about 10, about 25, or about 50 mg per day as measured in the amount of free Compound 1 or a maleate salt thereof.

In certain embodiments, the therapeutically effective amount of Compound 1 is ranging from about 1 to about 500, from about 2 to about 300, from about 5 to about 200, or from about 5 to about 100 mg per day as measured in the amount of free Compound 1 or a maleate salt thereof. In certain embodiments, the therapeutically effective amount of Compound 1 is about 5, about 10, about 25, about 50, about 100, about 200, or about 300 mg per day as measured in the amount of free Compound 1 or a maleate salt thereof. In certain embodiments, the therapeutically effective amount of Compound 1 is about 5, about 10, about 15, about 20, about 25, about 30, about 35, about 40, about 45, about 50, about 60, about 70, about 80, about 90, about 100, about 110, about 120, about 130, about 140, or about 150 mg per day as measured in the amount of free Compound 1 or a maleate salt thereof. In certain embodiments, the therapeutically effective amount of Compound 1 is about 5, about 10, about 25, about 50, about 100, about 200, or about 300 mg per day as measured in the amount of free Compound 1 or a maleate salt thereof. In certain embodiments, the therapeutically effective amount of Compound 1 is about 10, about 25, about 50, or about 200 mg per day as measured in the amount of free Compound 1 or a maleate salt thereof.

In certain embodiments, Compound 1, or a pharmaceutical acceptable solvate or hydrate thereof, is administered in a sufficient amount to provide an arithmetic mean area under the curve (AUC) of Compound 1 in the range from about 1 to about 500 ng·hr/mL, from about 2 to 500 ng·hr/mL, from about 5 to 500 ng·hr/mL, from about 5 to 200 ng·hr/mL, from about 5 to 100 ng·hr/mL, from about 5 to 50 ng·hr/mL, or from about 10 to 50 ng·hr/mL. In certain embodiments, Compound 1, or a pharmaceutical acceptable solvate or hydrate thereof, is administered in a sufficient amount to provide an arithmetic mean AUC of Compound 1 in the range from about 10 to about 200 ng·hr/mL.

In certain embodiments, Compound 1, or a pharmaceutical acceptable solvate or hydrate thereof, is administered in a sufficient amount to provide an arithmetic mean $AUC_\infty$ of Compound 1 in the range from about 1 to about 500 ng·hr/mL, from about 2 to 500 ng·hr/mL, from about 5 to 500 ng·hr/mL, from about 5 to 200 ng·hr/mL, from about 5 to 100 ng·hr/mL, from about 5 to 50 ng·hr/mL, or from about 10 to 50 ng·hr/mL. In certain embodiments, Compound 1, or a pharmaceutical acceptable solvate or hydrate thereof, is administered in a sufficient amount to provide an arithmetic mean $AUC_\infty$ of Compound 1 in the range from about 10 to about 200 ng·hr/mL.

In certain embodiments, Compound 1, or a pharmaceutical acceptable solvate or hydrate thereof, is administered in a sufficient amount to provide an arithmetic mean peak plasma concentration ($C_{max}$) of Compound 1 ranging from about 1 to about 500 ng/mL, from about 1 to about 200 ng/mL, from about 1 to about 100 ng/mL, from about 1 to about 50 ng/mL, from about 2 to about 50 ng/mL from about 5 to about 50 ng/mL, or from about 5 to about 20 ng/mL. In certain embodiments, Compound 1, or a pharmaceutical acceptable solvate or hydrate thereof, is administered in a sufficient amount to provide an arithmetic mean $C_{max}$ of Compound 1 ranging from about 5 to about 50 ng/mL, In certain embodiments, Compound 1, or a pharmaceutical acceptable solvate or hydrate thereof, is administered in a sufficient amount to provide an average steady-state plasma concentration of Compound 1 ranging from about 1 to about 500 ng/mL, from about 1 to about 200 ng/mL, from about 1 to about 100 ng/mL, from about 1 to about 50 ng/mL, from about 2 to about 50 ng/mL from about 2 to about 50 ng/mL, from about 2 to about 20 ng/mL, or from about 5 to about 20 ng/mL. In certain embodiments, Compound 1, or a pharmaceutical acceptable solvate or hydrate thereof, is administered in a sufficient amount to provide an average steady-state plasma concentration of Compound 1 ranging from about 5 to about 100 ng/mL.

In certain embodiments, Compound 1, or a pharmaceutical acceptable solvate or hydrate thereof, is administered in a sufficient amount to provide an average trough plasma concentration or average minimum concentration of Compound 1 ranging from about 0.01 to about 10 ng/mL, from about 0.05 to about 5 ng/mL, from about 0.1 to about 2 ng/mL, or from about 0.2 to about 1 ng/mL. In certain embodiments, Compound 1, or a pharmaceutical acceptable solvate or hydrate thereof, is administered in a sufficient amount to provide an average trough plasma concentration or average minimum concentration of Compound 1 ranging from about 0.2 to about 10 ng/mL.

In certain embodiments, the subject is a mammal. In certain embodiments, the subject is a human.

The methods provided herein encompass treating a subject regardless of patient's age, although some diseases or disorders are more common in certain age groups.

Depending on the disease to be treated and the subject's conditions, Compound 1 or a pharmaceutically acceptable salt thereof, or a pharmaceutical acceptable solvate or hydrate thereof, may be administered by an oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) route of administration.

Compound 1 or a pharmaceutically acceptable salt thereof, or a pharmaceutical acceptable solvate or hydrate thereof, may be formulated, alone or together, in a suitable dosage unit with pharmaceutically acceptable excipients, carriers, adjuvants and vehicles, appropriate for each route of administration. In one embodiment, Compound 1 or a pharmaceutically acceptable salt thereof, or a pharmaceutical acceptable solvate or hydrate thereof, is administered orally. In another embodiment, Compound 1 or a pharmaceutically acceptable salt thereof, or a pharmaceutical acceptable solvate or hydrate thereof, is administered parenterally. In yet another embodiment, Compound 1 or a pharmaceutically acceptable salt thereof, or a pharmaceutical acceptable solvate or hydrate thereof, is administered intravenously. In yet another embodiment, Compound 1 or a pharmaceutically acceptable salt thereof, or a pharmaceutical acceptable solvate or hydrate thereof, is administered intramuscularly. In yet another embodiment, Compound 1 or a pharmaceutically acceptable salt thereof, or a pharmaceutical acceptable solvate or hydrate thereof, is administered subcutaneously. In still another embodiment, Compound 1 or a pharmaceutically acceptable salt thereof, or a pharmaceutical acceptable solvate or hydrate thereof, is administered topically.

Compound 1 or a pharmaceutically acceptable salt thereof, or a pharmaceutical acceptable solvate or hydrate thereof, can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy,* supra; *Modified-Release Drug Delivery Technology,* 2nd Edition, Rathbone et al., Eds., Marcel Dekker, Inc.: New York, N.Y., 2008).

In one embodiment, Compound 1 is formulated in a dosage form for oral administration, which comprises Compound 1 or a pharmaceutically acceptable salt thereof, or a pharmaceutical acceptable solvate or hydrate thereof, and a pharmaceutically acceptable excipient.

The oral dosage can be provided in a solid, semisolid, or liquid dosage form. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), e.g., Compound 1 or a pharmaceutically acceptable salt thereof, or a pharmaceutical acceptable solvate or hydrate thereof, the oral dosage form can contain one or more pharmaceutically acceptable excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), and hydroxypropyl methyl cellulose (HPMC); microcrystalline celluloses, such as AVICEL-PH-101, AVICEL-PH-102, AVICEL-PH-103, AVICEL RC-581, and AVICEL-PH-105 (FMC Corp., Marcus Hook, Pa.); and mixtures thereof.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, such as peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof.

Suitable glidants include, but are not limited to, colloidal silicon dioxide, CAB-O-SIL® (Cabot Co. of Boston, Mass.), and asbestos-free talc.

Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye.

Suitable flavoring agents include, but are not limited to, natural flavors extracted from plants, such as fruits, and synthetic blends of compounds, which produce a pleasant taste sensation, such as peppermint and methyl salicylate.

Suitable sweetening agents include, but are not limited to, sucrose, lactose, mannitol, syrups, glycerin, and artificial sweeteners, such as saccharin and aspartame.

Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate.

Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

Suitable preservatives include, but are not limited to, glycerin, methyl and propylparaben, benzoic add, sodium benzoate and alcohol.

Suitable wetting agents include, but are not limited to, propylene glycol monostearate, sorbitan monooleate, diethylene glycol monolaurate, and polyoxyethylene lauryl ether.

Suitable solvents include, but are not limited to, glycerin, sorbitol, ethyl alcohol, and syrup. Suitable non-aqueous liquids utilized in emulsions include, but are not limited to, mineral oil and cottonseed oil.

Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The oral dosage form can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The oral dosage form can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The oral dosage form can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

The oral dosage form can be formulated as immediate or modified release dosage forms, including delayed-, sustained, pulsed-, controlled, targeted-, and programmed-release forms.

In one embodiment, Compound 1 is formulated in an oral dosage form, which comprises Compound 1 or a pharmaceutically acceptable salt thereof, or a pharmaceutical acceptable solvate or hydrate thereof, and a binder, a disintegrant, and a lubricant.

In another embodiment, Compound 1 is formulated in an oral dosage form, which comprises a maleate salt of Compound 1, or a pharmaceutical acceptable solvate or hydrate thereof, and a binder, a disintegrant, and a lubricant.

In yet another embodiment, Compound 1 is provided in an oral dosage, which comprises a maleate salt of Compound 1, or a pharmaceutical acceptable solvate or hydrate thereof; and a microcrystalline cellulose, sodium starch glycolate, and magnesium stearate.

In certain embodiments, the oral dosage form is provided as a tablet or capsule. In certain embodiments, the oral dosage form is provided as a tablet. In certain embodiments, the oral dosage form is provided as a capsule.

Compound 1, or a pharmaceutical acceptable solvate or hydrate thereof, can be delivered as a single dose such as, e.g., a single bolus injection, or oral tablets or pills; or over time such as, e.g., continuous infusion over time or divided bolus doses over time. Compound 1, or a pharmaceutical acceptable solvate or hydrate thereof, can be administered repetitively if necessary, for example, until the patient experiences stable disease or regression, or until the patient experiences disease progression or unacceptable toxicity. Stable disease or lack thereof is determined by methods known in the art, such as evaluation of patient symptoms and physical examination.

Compound 1, or a pharmaceutical acceptable solvate or hydrate thereof, can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of Compound 1, or a pharmaceutical acceptable solvate or hydrate thereof, is administration for one to six days per week, administration in cycles (e.g., daily administration for two to eight consecutive weeks, then a rest period with no administration for up to one week), or administration on alternate days.

In certain embodiments, Compound 1, or a pharmaceutical acceptable solvate or hydrate thereof, is cyclically administered to a patient. Cycling therapy involves the administration of an active agent for a period of time, followed by a rest for a period of time, and repeating this sequential administration. Cycling therapy can avoid or reduce the side effects of one of the therapies, and/or improves the efficacy of the treatment.

In certain embodiments, Compound 1, or a pharmaceutical acceptable solvate or hydrate thereof, is administered under fasted conditions. In certain embodiments, Compound 1, or a pharmaceutical acceptable solvate or hydrate thereof, is administered without a food. In certain embodiments, Compound 1, or a pharmaceutical acceptable solvate or hydrate thereof, is administered at least 10, 10, or 30 minutes, before a meal. In certain embodiments, Compound 1, or a pharmaceutical acceptable solvate or hydrate thereof, is administered at least 1, 2, or 3 hours after a meal.

In certain embodiments, each method provided herein further independently comprises the step of administering a second therapeutic agent.

Compound 1, or a pharmaceutical acceptable solvate or hydrate thereof, can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein also are kits which, when used by the medical practitioner, can simplify the administration of appropriate amounts of active ingredients to a subject. In certain embodiments, the kit provided herein includes a container and a dosage form of Compound 1.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); mmol (millimoles); h (hour or hours); min (minutes); and HPLC (high pressure liquid chromatography).

For all of the following examples, unless otherwise indicated, all temperatures are expressed in ° C. (degrees Centigrade).

Example 1

Phase I Evaluation of 3-((1-Cyclohexyl-4-oxo-8-(4-oxo-4-phenylbutyl)-1,3,8-triazaspiro[4.5]decan-3-yl)methyl)benzoic Acid Maleate A phase I randomized, double-blind, placebo-controlled, adaptive-design, single-ascending dose (SAD) and multiple-ascending dose (MAD) study was conducted in healthy human subjects to evaluate the safety, tolerability, pharmacokinetics (PK), pharmacodynamics (PD), food effect, and optimal oral dose of 3-((1-cyclohexyl-4-oxo-8-(4-oxo-4-phenylbutyl)-1,3,8-triazaspiro[4.5]decan-3-yl)methyl)benzoic acid maleate (hereinafter, "the Maleate Salt"). The SAD phase included an arm to evaluate food effect on the PK of the Maleate Salt. The SAD phase also evaluated the effect of the Maleate Salt on ECG parameters, including an assessment of QT-interval changes using exposure-response analysis.

The Maleate Salt was formulated in the study as immediate-release, hard gelatin capsules for oral administration. Each capsule contained 5 mg or 25 mg of the Maleate Salt, as well as microcrystalline cellulose NF (AVICEL® PH-102), sodium starch glycolate NF (EXPLOTAB®), and magnesium stearate NF, all filled into a size 3 hard gelatin capsule. A matching placebo containing the same amount of microcrystalline cellulose NF in place of the Maleate Salt was used in the study. The Maleate Salt capsules and matching placebo capsules were packaged in high-density polyethylene (HDPE) bottles with polypropylene caps and stored at controlled conditions per the USP.

A total of 54 subjects received at least 1 dose of the Maleate Salt, ranging from 5 mg to the maximum single PO dose of 300 mg. Six subjects received a maximum single PO dose of 300 mg and 5 subjects received a total of 900 mg of the Maleate Salt over 5-day period (100 mg BID for 4 days with single 100 mg on Day 5).

The SAD phase had 7 cohorts dosed at 5 mg (cohort 1), 10 mg (cohort 2), 25 mg (cohort 3), 50 mg (cohort 4), 100 mg (cohort 5), 200 mg (cohort 6), and 300 mg (cohort 7) of the Maleate Salt. In each cohort, there were 6 active- and 2 placebo-treated subjects. Subjects were administered the Maleate Salt in the fasting state with 1 exception: subjects in the 25 mg cohort (cohort 3) received the Maleate Salt while fasting and again after a high-fat breakfast to determine food effect on PK.

Mean plasma concentration-time profiles for 3-((1-cyclohexyl-4-oxo-8-(4-oxo-4-phenylbutyl)-1,3,8-triazaspiro[4.5]decan-3-yl)methyl)benzoic acid (hereinafter, "the Compound") following a single PO dose of the Maleate Salt are shown in FIG. 1. The concentration-time profiles show rapid absorption and rapid elimination over 24 h. PK parameters of the Maleate Salt following single PO doses are summarized in Table 1 below.

Arithmetic mean $C_{max}$ ranged from 2.1 ng/mL at the 5 mg dose level to 191.8 ng/mL at the 300 mg dose level. Median $T_{max}$ was about 1.1 h. Arithmetic mean $T_{1/2}$ in the fasted subjects was approximately 1.6 h at the 5 and 10 mg dose levels. Arithmetic mean $T_{1/2}$ in fasted subjects ranged from approximately 3.1 to 6.0 h at the 25 to 300 mg dose levels. Arithmetic mean $T_{1/2}$ in fasted subjects was approximately 4.0 h across all cohorts in the SAD phase. Exposure to the Maleate Salt is approximately proportional to the dose administered in the SAD phase under fasted conditions.

Figure 2:
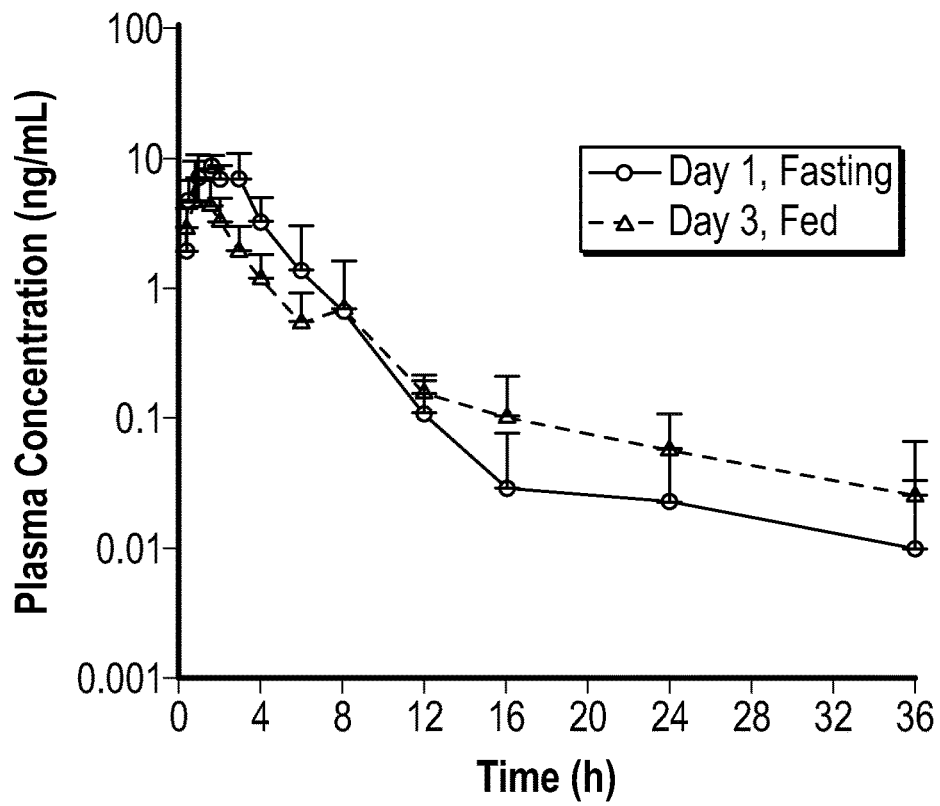
FIG. 2 shows mean plasma concentration-time profiles of 3-((1-cyclohexyl-4-oxo-8-(4-oxo-4-phenylbutyl)-1,3,8-triazaspiro[4.5]decan-3-yl)methyl)benzoic acid in fasting and fed subjects following a single PO dose.

In evaluating food effect on the PK of the Maleate Salt, subjects on Day 1 in cohort 3 were administered a single dose of the Maleate Salt at 25 mg or placebo in the fasted state. On Day 3, the same subjects received an identical dose 30 minutes after consumption of a standardized, high-fat, high-calorie breakfast. Mean plasma concentration-time profiles for the Compound in the fasted and fed states are shown in FIG. 2. Consumption of the high-fat meal prior to dosing reduced the extent of absorption ($C_{max}$ and AUC), but did not alter $T_{max}$ (see Table 1 above).

TABLE 1

| Dose (mg) | Fed State | $T_{max}$ (h) | $C_{max}$ (ng/mL) | $AUC_{last}$ (h · ng/mL) | $AUC_\infty$ (h · ng/mL) | $T_{1/2}$ (h) |
|---|---|---|---|---|---|---|
| 5 | Fasted | 0.83 | 2.1 | 4.3 | 4.5 | 1.6 |
| 10 | Fasted | 1.21 | 6.2 | 12.9 | 13.1 | 1.6 |
| 25 | Fasted | 1.80 | 10.5 | 30.5 | 30.4 | 6.0 |
|  | Fed | 2.20 | 6.7 | 17.6 | 17.2 | 7.0 |
| 50 | Fasted | 1.04 | 22.0 | 53.2 | 56.7 | 3.1 |
| 100 | Fasted | 1.78 | 48.3 | 103.8 | 180.2 | 5.4 |
| 200 | Fasted | 1.24 | 105.6 | 240.1 | 242.4 | 5.4 |
| 300 | Fasted | 1.88 | 191.8 | 421.3 | 446.5 | 5.1 |

The MAD phase had 2 cohorts dosed at 50 and 100 mg of the Maleate Salt. In each cohort, there were 6 active- and 2 placebo-treated subjects. The Maleate Salt was administered to fasting subjects BID (morning and evening) on Days 1 through 4 and as a single morning dose on Day 5.

Figure 3:
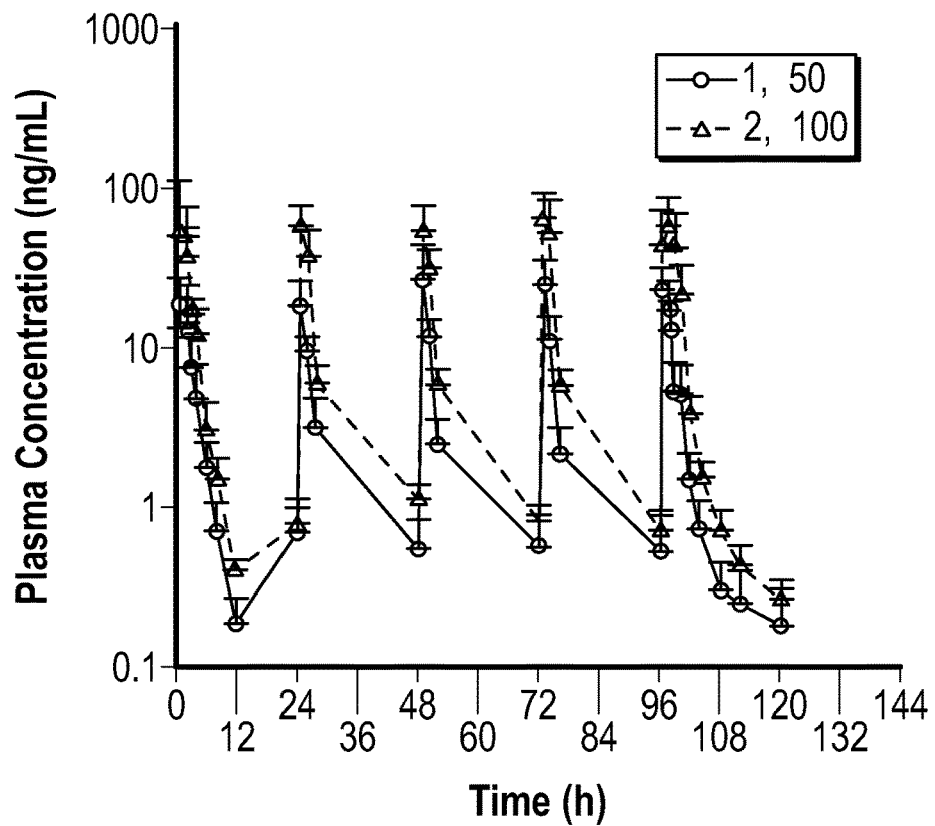
FIG. 3 shows mean plasma concentration-time profiles of 3-((1-cyclohexyl-4-oxo-8-(4-oxo-4-phenylbutyl)-1,3,8-triazaspiro[4.5]decan-3-yl)methyl)benzoic acid in fasting subjects following multiple PO doses.

Mean plasma concentration-time profiles for the Compound in the MAD phase are shown in FIG. 3. Similar to the SAD phase, plasma concentration-time profiles in the MAD phase showed rapid absorption and rapid elimination of the Compound. In addition, there was little accumulation apparent with the Maleate Salt at 50 or 100 mg BID dosing (less than 40% for $C_{max}$ and less than 30% for $AUC_{12}$). The mean AI was 1.89 and 1.38 at the 50 and 100 mg BID dose levels, respectively. PK parameters of the Maleate Salt for the MAD phase are summarized in Table 2 below.

On Day 1, mean $T_{1/2}$ was approximately 2 h for both 50 and 100 mg BID doses. On Day 5, mean $T_{1/2}$ was 11.0 and 6.2 h following 50 and 100 mg BID doses, respectively. For $T_{1/2}$ determination, the plasma samples for Day 1 were only collected to 12 h, whereas the plasma samples for Day 5 were collected to 24 h. A summary of steady-state PK parameters on Day 5 of the MAD phase are provided in Table 4 below.

TABLE 3

| Dose (mg) | Dose Day | $T_{max}$ (h) | $C_{max}$ (ng/mL) | $T_{last}$ (h) | $C_{last}$ (ng/mL) | $AUC_{12}$ (h · ng/mL) | $T_{1/2}$ (h) |
|---|---|---|---|---|---|---|---|
| 50 | 1 | 1.55 | 23.3 | 12.0 | 0.20 | 53.6 | 2.0 |
|  | 5 | 1.17 | 31.2 | 24.0 | 0.18 | 58.1 | 11.0 |
| 100 | 1 | 1.03 | 71.5 | 12.0 | 0.42 | 152.3 | 2.1 |
|  | 5 | 1.53 | 71.6 | 24.0 | 0.28 | 200.5 | 6.2 |

TABLE 4

| Dose (mg) | $T_{min}$ (h) | $C_{min}$ (ng/mL) | $C_{av,\ ss}$ (ng/mL) | AI |
|---|---|---|---|---|
| 50 | 8.0 | 0.32 | 4.84 | 1.89 |
| 100 | 4.8 | 0.65 | 16.71 | 1.38 |

Example 2

Clinical PD Evaluation of 3-((1-Cyclohexyl-4-oxo-8-(4-oxo-4-phenylbutyl)-1,3,8-triazaspiro[4.5]decan-3-yl)methyl)benzoic Acid Maleate In the same phase I study, serum prolactin concentrations were evaluated as a marker of pharmacologic activity ($D_2$ receptor target engagement). Prolactin is primarily secreted from lactotroph cells of the anterior pituitary gland, and the release of prolactin from these cells is under inhibitory control by DA. Fitzgerald and Dinan, *J. Psychopharmacol.* 2008, 22, 12-19.

Figure 4:
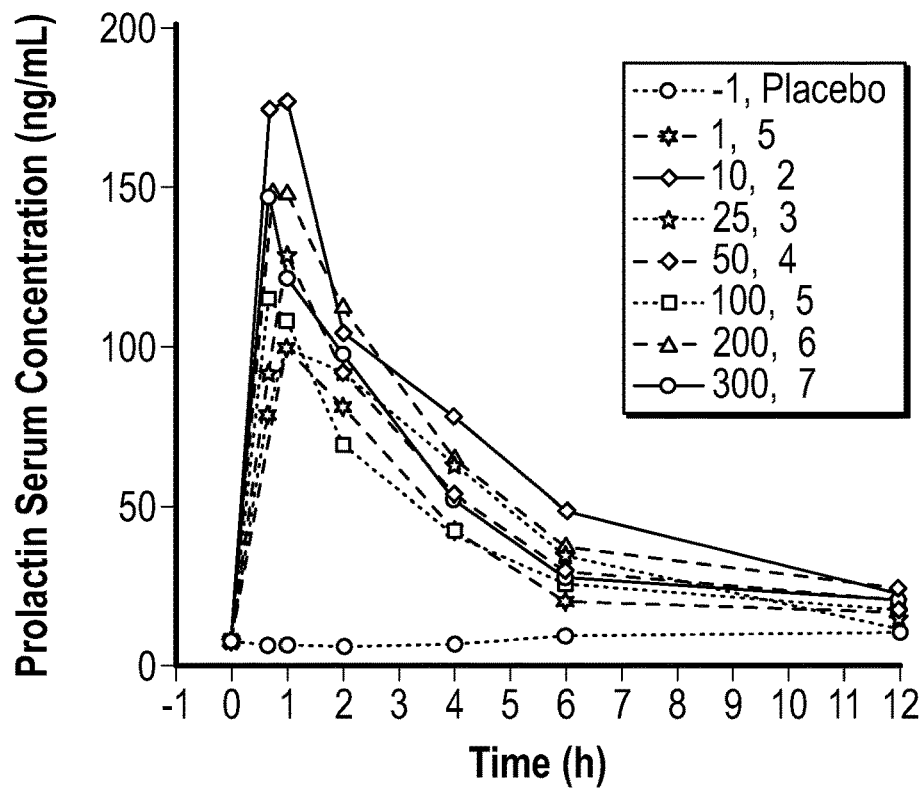
FIG. 4 shows mean serum prolactin concentration versus nominal time in fasting subjects following a single PO dose of 3-((1-cyclohexyl-4-oxo-8-(4-oxo-4-phenylbutyl)-1,3,8-triazaspiro[4.5]decan-3-yl)methyl)benzoic acid maleate.
Figure 5:
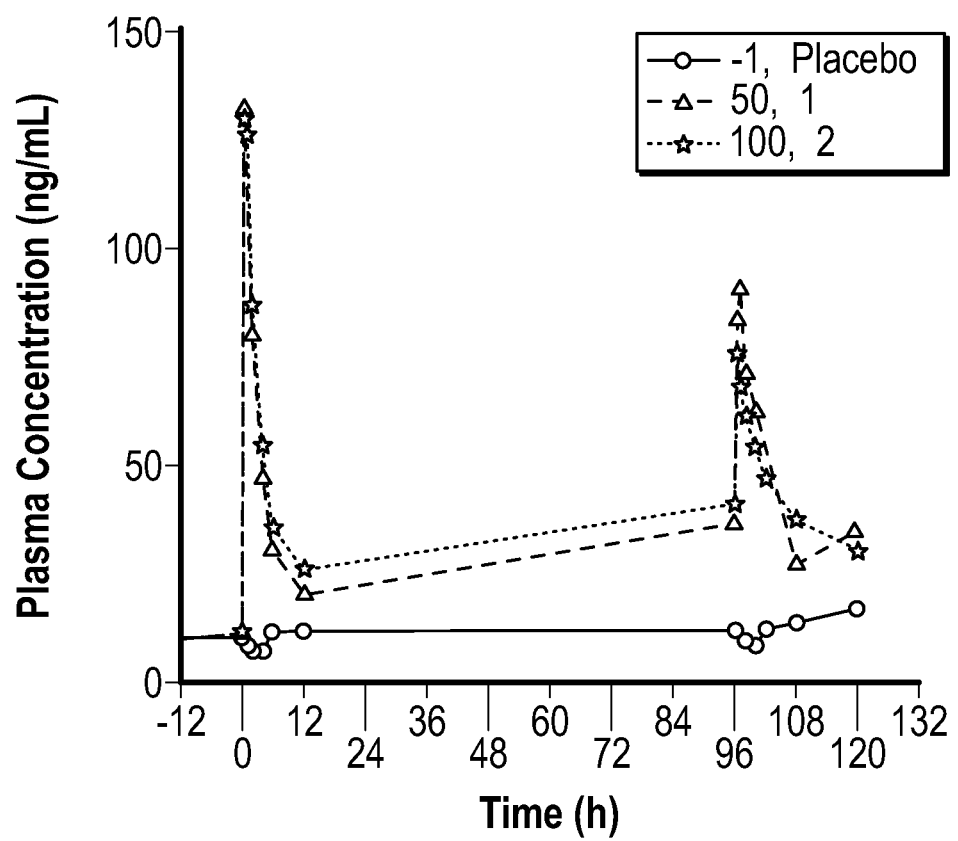
FIG. 5 shows mean serum prolactin concentration versus nominal time in fasting subjects following multiple PO doses of 3-((1-cyclohexyl-4-oxo-8-(4-oxo-4-phenylbutyl)-1,3,8-triazaspiro[4.5]decan-3-yl)methyl)benzoic acid maleate.

Concentration-time profiles of serum prolactin for the SAD and MAD phases are shown in FIGS. 4 and 5, respectively. Following oral administration of the Maleate Salt, serum prolactin concentration increased rapidly. The median serum prolactin $T_{max}$ was approximately 1.1 h and ranged from 0.7 to 2 h across all 48 single-dose administration of the Maleate Salt. The increases were substantial compared to placebo. The prolactin response was maximal at the 10 mg dose of the Maleate Salt in the SAD phase. In the MAD phase, there was little if any accumulation in serum prolactin after BID dosing for 5 days.

Example 3

Evaluation of 3-((1-Cyclohexyl-4-oxo-8-(4-oxo-4-phenylbutyl)-1,3,8-triazaspiro[4.5]decan-3-yl)methyl)benzoic Acid Maleate A phase I randomized, double-blind and open-label, placebo and active-comparator controlled study is conducted to evaluate the safety, tolerability, and pharmacokinetics (PK)/pharmacodynamics (PD) of, and food effect on 3-((1-cyclohexyl-4-oxo-8-(4-oxo-4-phenylbutyl)-1,3,8-triazaspiro[4.5]decan-3-yl)methyl)benzoic acid maleate ("the Compound") in subjects with gastroparesis, in particular, those with diabetes mellitus and gastroparesis (DG) or with idiopathic gastroparesis (IG). The effect of the Compound on gastric emptying (GE) is also determined.

The study enrolls approximately 48 subjects. The study is conducted in two parts: Part 1 (double-blind) and Part 2 (open-label). Subjects in Part 1 are randomly assigned (by chance, like flipping a coin) to one of the four treatment groups, Groups 1 to 4. Subjects in Group 1 each receive 5 mg of the Compound in a capsule orally, twice daily under fasted conditions for up to 9 days. Subjects in Group 2 each receive 25 mg of the Compound in a capsule orally, twice daily under fasted conditions for up to 9 days. Subjects in Group 3 each receive 100 mg of the Compound in a capsule orally, twice daily under fasted conditions for up to 9 days. Subjects in Group 4 each receive a placebo in a matching capsule orally, twice daily under fasted conditions for up to 9 days. Gastrointestinal emptying is evaluated following a test meal using a $^{13}C$-Spirulina gastric emptying breath test (GEBT), and GI emptying and motility are evaluated using SmartPill technology. Blood samples for assessment of the Compound concentrations are collected at scheduled time points from predose on Day 1 to 48 hours after Day 7 dose. Blood samples for assessment of prolactin concentrations in serum are collected at screening and scheduled time points from Day-2 to 48 hours after Day 7 dose. Subject randomization is stratified by the underlying condition, i.e., DG versus IG. The assignments remain undisclosed to the subjects and study doctors during the study (unless there is an urgent medical need).

All subjects who complete Part 1 of the study are eligible for enrollment in Part 2. In Part 2, approximately 6 subjects who completed Part 1 are enrolled to receive 25 mg of the Compound with or without food in an open-label crossover design over 2 periods. A minimum 7-day washout separates the doses in each period. Blood samples for assessment of the Compound concentrations are collected from predose to 48 hours after each dose of the Compound. Furthermore, up to an additional 12 subjects who completed Part 1 of the study are enrolled in the evaluation of the Compound vs active comparator metoclopramide to confirm the responsiveness of the GEBT test. Subjects are blinded to treatment until all subjects have completed Part 1. Blood samples for assessment of the Compound or metoclopramide concentrations are collected at scheduled time points from predose on Day 1 to 48 hours postdose.

The overall time to participate in this study is approximately 8 weeks. The subjects make a final visit to the clinic 10-14 days after receiving their last dose of study drug for a follow-up assessment.

In both Parts 1 and 2, the subjects are monitored for vital signs and treatment-emergent adverse events (TEAEs); and by physical examination, electrocardiograms, and safety laboratory tests.

In Part 1, change from baseline in serum prolactin on Day 1 at time of first occurrence of maximum plasma concentration ($T_{max}$) for the Compound is determined. In Part 1, change from baseline in GEBT (gastric emptying breath test) gastric half-emptying time as measured by the $^{13}C$ spirulina GEBT on Day 1 and 7 is determined. The GEBT is a nonradioactive, noninvasive, orally administered test for measuring the rate of solid phase gastric emptying (GE) in adults. The GEBT measures how fast solid food moves from the stomach to the small intestine during the digestive process and aids in the diagnosis of delayed stomach emptying (GP). GE half-emptying time is the time for half of the ingested solids to leave the stomach. This value was measured by the $^{13}C$ spirulina GEBT.

In Part 1, percent change from baseline in GE time as measured by the SmartPill on Day 7 is determined. SmartPill is an ingestible capsule that measures pressure, potential of hydrogen (pH) and temperature as it travels through the gastrointestinal (GI) tract to assess GI motility. SmartPill eliminates radiation exposure and is the only motility test that provides a complete transit profile of the GI tract.

In Part 1, PK parameters for the Compound, including area under the plasma concentration-time curve ($AUC_T$) from 0 to 48 hours over the dosing interval, maximum observed plasma concentration (Cmax), time to reach the maximum plasma concentration ($T_{max}$), terminal disposition phase half-life ($T_{1/2Z}$), and observed plasma concentration at the end of dosing interval ($C_{trough}$) are determined. In Part 2, area under the plasma concentration-time curve from time 0 to infinity ($AUC_\infty$) is determined.

Eligible subjects for the study are the ones between 18 and 65 years old with a documented diagnosis of DG or IG. Also the eligible subjects have a body mass index (BMI) greater than or equal to (>=) 18 and less than or equal to (<=) 35 kilogram per square meter (kg/m$^2$) at the screening visit. The eligible subjects are nonsmokers who have not used tobacco or nicotine-containing products (example, nicotine patch) for at least 6 months prior to trial drug administration of the initial dose of trial drug/invasive procedure.

The eligible subjects have symptoms for GP (that is, chronic postprandial fullness, abdominal pain, postprandial nausea, vomiting, loss of appetite and/or early satiety) the past 3 months, and has documented slow GE, with delayed GE by GEBT at the screening defined as >=80th percentile. If the eligible subjects have had a documented scintigraphy or GEBT within the last 12 months that confirms the diagnosis of delayed GE, a screening GEBT would not be required. The eligible subjects have nausea subscale (of American Neurogastroenterology and Motility Society Gastroparesis Cardinal Symptom Index-Daily Diary [ANMS-GCSI-DD]) symptom score>=2 at least 3 of 7 days during the screening. The eligible subjects have hemoglobin A1c (HBA1c) less than (<) 10 percent (%) (for diabetes mellitus only).

The subjects who have acute severe gastroenteritis and pronounced dehydration in the past 48 hours prior to the screening, gastric pacemaker, chronic parenteral feeding or persistent severe vomiting are excluded from the study. Also excluded are those who have a known disturbance of small intestinal absorption, exocrine pancreatic function, liver metabolism, and pulmonary function; or who have a history of anorexia nervosa or bulimia, or previous history of bezoars (the presence of retained liquid, bile, or small amounts of poorly organized food residue is permitted); or difficulty swallowing solid food or pills; or prior surgery involving the luminal GI tract (cholecystectomy, appendectomy, and hysterectomy are permitted if performed greater than (>) 3 months prior to SmartPill test). The subjects who have any abdominal or pelvic surgery within the past 3 months; or known or history of inflammatory bowel disease; or history of diverticulitis, diverticular stricture, and other intestinal strictures; or had major surgery, donated or lost 1 unit of blood (approximately 500 milliliter [mL]) within 4 weeks prior to the pretrial (screening) visit milligram per deciliter (mg/dL) (14.99 millimole per liter [mmol/L]) during any visit up to and including the randomization visit (Period 1 Day 1 predose) are also excluded. The subjects who have had diabetic ketoacidosis (within the prior 4 weeks) are excluded.

Example 4

Phase IIb Evaluation of the Efficacy and Safety of 3-((1-Cyclohexyl-4-oxo-8-(4-oxo-4-phenylbutyl)-1,3,8-triazaspiro[4.5]decan-3-yl)methyl)benzoic Acid Maleate in Subjects with Symptomatic Idiopathic or Diabetic Gastroparesis A multicenter, randomized, double-blind, placebo-controlled, parallel-group, Phase IIb study is conducted to evaluate the efficacy and safety of twice-daily oral administration of a peripherally acting dopamine receptor D2/D3 antagonist, 3-((1-cyclohexyl-4-oxo-8-(4-oxo-4-phenylbutyl)-1,3,8-triazaspiro[4.5]decan-3-yl)methyl)benzoic acid maleate ("the Compound"), for the treatment of adult subjects with symptomatic idiopathic or diabetic gastroparesis.

The study enrolls approximately 280 subjects. Eligible subjects for the study are adult men and women aged 18 to 85 years, inclusive, and with body mass index (BMI)≥19 to ≤40 kg/m$^2$ inclusive. The eligible subjects should have experienced symptoms of gastroparesis (e.g., postprandial fullness, nausea, vomiting, upper abdominal pain, and early satiety (at least intermittently)) for at least 3 months before screening as assessed by a physician. The eligible subjects must have confirmed delayed gastric emptying at screening; delayed gastric emptying by GEBT is defined as $t_{1/2}$≥79 min (80th percentile). The eligible subjects must have an average composite ANMS GCSI-DD (the American Neurogastroenterology and Motility Society Gastroparesis Cardinal Symptom Index-Daily Diary) symptom score≥2 during the 7 days before randomization. The predominant symptom experienced by subjects must not be abdominal pain. The eligible subjects must experience nausea: nausea subscale (of ANMS GCSI-DD) symptom score≥2 at least 4 of 7 days or an average nausea subscale symptom≥2 during the 7 days before randomization. Nausea symptoms must not be attributable to a central disorder (e.g., motion sickness, glaucoma, menstrual cycles, or migraine headache). The eligible subjects with diabetes mellitus must have glycosylated hemoglobin (HbA1c)≤11% at screening and before randomization. Given the biological variability of glycemic parameters, the eligible subjects with a value that does not meet the above criteria, but is within 0.2% HbA1c of the qualifying range may, at the discretion of the investigator have a repeat determination performed at Visit 2 and used as a qualifying parameter in lieu of the original value.

Subjects attend a study site for a screening/consent visit (Visit 1, Day-35), when their consent is obtained and general eligibility to participate in the study is reviewed. Subjects discontinue all excluded medication and return to the site up to approximately 2 weeks later to perform a 4-hour $^{13}$C-Spirulina GEBT (Visit 2). Subjects who are not taking any medications at the screening visit that require washout may attend the clinic for Visit 2 earlier than 2 weeks. An 8-hour fast is required before the GEBT. Subjects have a blood sample taken to check their laboratory values and then return within 7 days after the GEBT visit to confirm their eligibility (Visit 3, Day-14). Once eligibility is confirmed at this visit, eligible subjects are instructed on the use of an electronic patient reported outcomes (ePRO) tool for collecting gastroparesis symptom data. The instrument used is the American Neurogastroenterology and Motility Society Gastroparesis Cardinal Symptom Index-Daily Diary (ANMS GCSI-DD). The subjects record their symptoms once daily (in the evening) and return to the clinic approximately 2 weeks later to assess their gastroparesis symptom eligibility based on the ANMS GCSI-DD (Visit 4, Randomization). The subjects need to be compliant with completing the ANMS GCSI-DD, defined as ≥80% diary completions, during the 2-week symptom assessment period.

The overall time to participate in this study is 17 weeks. The eligible subjects are randomly assigned to one of four treatment groups (in 1:1:1:1 ratio), each group stratified by idiopathic gastroparesis (IG) or diabetic gastroparesis (DG) (minimum 30 subjects per indication per arm). The assignments remain undisclosed to the subjects and study doctors during the study (unless there is an urgent medical need). Subjects in Treatment Group 1 each receive 5 mg of the Compound in a capsule orally, twice daily for twelve weeks.

Subjects in Treatment Group 2 each receive 25 mg of the Compound in a capsule orally, twice daily for twelve weeks. Subjects in Treatment Group 3 each receive 50 mg of the Compound in a capsule orally, twice daily for twelve weeks. Subjects in Treatment Group 4 each receive a placebo in a matching capsule orally, twice daily for twelve weeks. All the subjects are asked to take two capsules at the same time each day throughout the study. Capsules are taken on an empty stomach (at least 2 hours of fasting except for water and juice); 1 capsule in the morning approximately 1 hour before the first meal of the day and another capsule in the evening approximately 1 hour before the main last meal of the day, at a regular dose interval. The subjects take their first study medication at the site on the morning of the Randomization Visit and take their morning study medication in clinic at Visits 5, 6, and 7. The subjects complete the ANMS GCSI-DD daily for 12 weeks and attend the clinic at Weeks 4 (Visit 5), 8 (Visit 6), and 12 (Visit 7) and have additional GEBTs performed after 4 (Visit 5) and 12 (Visit 7) weeks treatment. At each visit following randomization, PK samples are taken both predose and postdose and blood samples for exploratory biomarker analysis are taken from Visit 2 through Visit 7. A safety follow-up phone call are made approximately 40 days after last dose of study medication.

During the study, four gastroparesis-related symptoms (nausea, early satiety, postprandial fullness, and upper abdominal pain) are analyzed by ANMS GCSI-DD. The severity scores of four gastroparesis-related symptoms (nausea, early satiety, postprandial fullness, and upper abdominal pain) range from 0 (none) to 4 (very severe). An ANMS GCSI-DD composite score (nausea, early satiety, postprandial fullness, and upper abdominal pain) is then calculated for each subject. Two additional symptoms (vomiting (frequency) and bloating) are also analyzed by ANMS GCSI-DD. The severity scores of the two symptoms (vomiting (frequency) and bloating) also range from 0 (none) to 4 (very severe). An ANMS GCSI-DD composite score (nausea, early satiety, postprandial fullness, upper abdominal pain, bloating, and vomiting) is then calculated for each subject.

Two additional instruments, PAGI-SYM (the Patient Assessment of Upper Gastrointestinal Disorders-Symptom Severity Index) and GEBT, are also used in the study. PAGI-SYM is a 20-item self-reported questionnaire that measures symptom severity of upper gastrointestinal disorders across six subscales (nausea/vomiting, fullness/early satiety, bloating, upper abdominal pain, lower abdominal pain, heartburn/regurgitation). GEBT is a nonradioactive, noninvasive, orally administered test for measuring the rate of solid phase gastric emptying (GE) in adults. GEBT measures how fast solid food moves from the stomach to the small intestine during the digestive process and aids in the diagnosis of delayed stomach emptying (GP). GE half-emptying time is the time for half of the ingested solids to leave the stomach. This value is measured by the $^{13}C$ spirulina GEBT.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or alleviating one or more symptoms of gastroparesis or a disorder characterized by delayed gastric emptying in a subject, or increasing the serum prolactin concentration in a subject, comprising administering to the subject a therapeutically effective amount of a salt of 3-((1-cyclohexyl-4-oxo-8-(4-oxo-4-phenylbutyl)-1,3,8-triazaspiro[4.5]decan-3-yl)methyl)benzoic acid and maleic acid.

2. The method of claim 1, wherein the gastroparesis is diabetic or idiopathic gastroparesis.

3. The method of claim 1, wherein the one or more symptoms are abdominal pain, belching, bloating, early satiety, epigastric pain or discomfort, excess gas, heartburn, loss of appetite, nausea, postprandial fullness, regurgitation, swollen abdomen, vomiting, or a combination thereof.

4. The method of claim 1, wherein the one or more symptoms are abdominal pain, bloating, early satiety, epigastric pain or discomfort, nausea, postprandial fullness, vomiting, or a combination thereof.

5. The method of claim 1, wherein the one or more symptoms are belching, bloating, heartburn, indigestion, nausea, regurgitation, vomiting, or a combination thereof.

6. The method of claim 1, wherein the therapeutically effective amount of the salt of 3-((1-cyclohexyl-4-oxo-8-(4-oxo-4-phenylbutyl)-1,3,8-triazaspiro[4.5]decan-3-yl) methyl)benzoic acid and maleic acid is the amount sufficient to increase the serum prolactin level to a concentration ranging from about 10 to about 500 ng/mL.

7. The method of claim 6, wherein the therapeutically effective amount of the salt of 3-((1-cyclohexyl-4-oxo-8-(4-oxo-4-phenylbutyl)-1,3,8-triazaspiro[4.5]decan-3-yl) methyl)benzoic acid and maleic acid is the amount sufficient to increase the serum prolactin level to a concentration ranging from about 50 to about 200 ng/mL.

8. The method of claim 1, wherein the molar ratio of the maleic acid to 3-((1-cyclohexyl-4-oxo-8-(4-oxo-4-phenylbutyl)-1,3,8-triazaspiro[4.5]decan-3-yl)methyl)benzoic acid is about 1.

9. The method of claim 1, wherein the therapeutically effective amount is ranging from about 1 to about 250 mg per day as measured in the amount of 3-((1-cyclohexyl-4-oxo-8-(4-oxo-4-phenylbutyl)-1,3,8-triazaspiro[4.5]decan-3-yl)methyl)benzoic acid or the salt.

10. The method of claim 9, wherein the therapeutically effective amount is ranging from about 5 to 200 mg per day as measured in the amount of 3-((1-cyclohexyl-4-oxo-8-(4-oxo-4-phenylbutyl)-1,3,8-triazaspiro[4.5]decan-3-yl) methyl)benzoic acid or the salt.

11. The method of claim 9, wherein the therapeutically effective amount is about 10, about 25, about 50, or about 100 mg per day as measured in the amount of 3-((1-cyclohexyl-4-oxo-8-(4-oxo-4-phenylbutyl)-1,3,8-triazaspiro[4.5]decan-3-yl)methyl)benzoic acid or the salt.

12. The method of claim 1, wherein the therapeutically effective amount is the amount sufficient to provide an arithmetic mean $AUC_\infty$ of 3-((1-cyclohexyl-4-oxo-8-(4-oxo-4-phenylbutyl)-1,3,8-triazaspiro[4.5]decan-3-yl) methyl)benzoic acid ranging from about 1 to about 500 ng·hr/mL.

13. The method of claim 12, wherein the therapeutically effective amount is the amount sufficient to provide an arithmetic mean $AUC_\infty$ of 3-((1-cyclohexyl-4-oxo-8-(4-oxo-4-phenylbutyl)-1,3,8-triazaspiro[4.5]decan-3-yl) methyl)benzoic acid ranging from about 10 to about 200 ng·hr/mL.

14. The method of claim 1, wherein the therapeutically effective amount is the amount sufficient to provide an arithmetic mean peak plasma concentration ($C_{max}$) of 3-((1-cyclohexyl-4-oxo-8-(4-oxo-4-phenylbutyl)-1,3,8-triazaspiro[4.5]decan-3-yl)methyl)benzoic acid ranging from about 1 to about 500 ng/mL.

15. The method of claim 12, wherein the therapeutically effective amount is the amount sufficient to provide an arithmetic mean peak plasma concentration ($C_{max}$) of 3-((1-cyclohexyl-4-oxo-8-(4-oxo-4-phenylbutyl)-1,3,8-triazaspiro[4.5]decan-3-yl)methyl)benzoic acid ranging from about 5 to about 50 ng/mL.

16. The method of claim 1, wherein the therapeutically effective amount is the amount sufficient to provide an average steady-state plasma concentration of 3-((1-cyclohexyl-4-oxo-8-(4-oxo-4-phenylbutyl)-1,3,8-triazaspiro[4.5]decan-3-yl)methyl)benzoic acid ranging from about 1 to about 500 ng/mL.

17. The method of claim 16, wherein the therapeutically effective amount is the amount sufficient to provide an average steady-state plasma concentration of 3-((1-cyclohexyl-4-oxo-8-(4-oxo-4-phenylbutyl)-1,3,8-triazaspiro[4.5]decan-3-yl)methyl)benzoic acid ranging from about 5 to about 100 ng/mL.

18. The method of claim 1, wherein the therapeutically effective amount is the amount sufficient to provide an average trough plasma concentration of 3-((1-cyclohexyl-4-oxo-8-(4-oxo-4-phenylbutyl)-1,3,8-triazaspiro[4.5]decan-3-yl)methyl)benzoic acid ranging from about 0.01 to about 50 ng/mL.

19. The method of claim 18, wherein the therapeutically effective amount is the amount sufficient to provide an average trough plasma concentration of 3-((1-cyclohexyl-4-oxo-8-(4-oxo-4-phenylbutyl)-1,3,8-triazaspiro[4.5]decan-3-yl)methyl)benzoic acid ranging from about 0.2 to about 10 ng/mL.

20. The method of claim 1, wherein the salt of 3-((1-cyclohexyl-4-oxo-8-(4-oxo-4-phenylbutyl)-1,3,8-triazaspiro[4.5]decan-3-yl)methyl)benzoic acid and maleic acid is administered orally or parenterally.

21. The method of claim 20, wherein the salt of 3-((1-cyclohexyl-4-oxo-8-(4-oxo-4-phenylbutyl)-1,3,8-triazaspiro[4.5]decan-3-yl)methyl)benzoic acid and maleic acid is administered under fasted conditions.

22. The method of claim 21, wherein the salt of 3-((1-cyclohexyl-4-oxo-8-(4-oxo-4-phenylbutyl)-1,3,8-triazaspiro[4.5]decan-3-yl)methyl)benzoic acid and maleic acid is administered at least 30 minutes before a meal.

23. The method of claim 21, wherein the salt of 3-((1-cyclohexyl-4-oxo-8-(4-oxo-4-phenylbutyl)-1,3,8-triazaspiro[4.5]decan-3-yl)methyl)benzoic acid and maleic acid is administered at least 1 hour after a meal.

\* \* \* \* \*